United States Patent [19] [11] 4,399,032
Mott [45] Aug. 16, 1983

[54] CHROMATOGRAPHIC COLUMN TERMINATOR ELEMENT AND ASSEMBLY

[76] Inventor: Lambert H. Mott, Spring La., Farmington Industrial Park, Farmington, Conn. 06032

[21] Appl. No.: 421,340

[22] Filed: Sep. 22, 1982

[51] Int. Cl.³ ............................................. B01D 15/08
[52] U.S. Cl. ................................. 210/198.2; 210/510; 55/386; 55/523
[58] Field of Search ...................... 210/198.2, 488, 489, 210/492, 510, 490; 55/386, 523

[56] References Cited

U.S. PATENT DOCUMENTS

| | | | |
|---|---|---|---|
| 2,723,756 | 11/1955 | Miller | 55/386 |
| 3,310,932 | 3/1967 | Melpolder | 55/386 |
| 3,398,512 | 8/1968 | Perkins | 55/386 |
| 3,790,475 | 2/1974 | Eaton | 210/198.2 |
| 3,855,130 | 12/1974 | Randau | 55/386 |
| 4,026,803 | 5/1977 | Abrahams | 210/198.2 |
| 4,354,932 | 10/1982 | McNeil | 55/386 |

Primary Examiner—Ernest G. Therkorn
Attorney, Agent, or Firm—Prutzman, Kalb, Chilton & Alix

[57] ABSTRACT

A porous sintered metal chromatographic column terminator element is disclosed comprising a relatively low density central disc portion, an integral relatively high density rim portion peripherally circumscribing the central portion and an interface zone that integrally joins the rim and central portions. The relatively flat faces of the rim and central portions are essentially coplanar but are separated and delineated by a channel at the surface of the interface zone intermediate said coplanar faces. The integral porous element exhibits a permeability ratio between the central disc portion and the rim portion of at least 3:1. Additionally, the central portion exhibits a density up to about 70 percent of the density of solid material of the same composition while the density of the rim portion is greater than that of the central portion and is up to about 95 percent of that of solid material of the same composition. The outer rim of the element provides an excellent seal with the packed tube of the chromatographic column to prevent side leakage. At the same time the element achieves improved efficiency of the chromatographic column.

9 Claims, 3 Drawing Figures

CHROMATOGRAPHIC COLUMN TERMINATOR ELEMENT AND ASSEMBLY

TECHNICAL FIELD

The present invention relates generally to a chromatographic column terminator assembly and is more particularly concerned with a new and improved assembly having a unique porous terminator element therein.

BACKGROUND

As is well known, chromatography is based on the principle that different substances within a mixture can be separated from one another and and concentrated into zones by passing the mixture through a two phase system. One phase of the system, such as a gas or liquid phase, acts as a carrier for the mixture while the other phase, such as solid granular absorbent powder, exerts a differential restraining force on the components of the mixture to cause separation and/or stratification thereof.

When using chromatographic columns to separate closely related complex substances, a sample of the material to be separated is fed through the granular absorbent packed within a long column. As the sample flows through the column the different components thereof separate and stratify so that they reach the exit end of the column in a sequential fashion. Such columns normally consist of tubes, such as stainless steel tubes, that are tightly packed with a very fine grain powdered material having a large specific surface area. Exposure of the sample to this large specific surface area causes some components of the sample to be restrained in their flow, thereby permitting the column to provide distinct and reproducible separation and resolution of the sample into its component parts as it travels through the column.

In order to obtain highly efficient separation or fractionation of the component parts of the sample, particularly where one component is present in only a small amount and is close chromatographically to a major component, it is essential to provide uniform exposure of the sample across the entire cross-sectional face of the column. Maximum efficiency of a chromatographic column is obtained when the sample enters the packed column with a uniform flow profile across the entire face of the column, when the profile proceeds through the column at a uniform rate and when the carrier and sample progress in substantially a stratified or laminar fashion. If the sample is not uniformly spread across the face of the column, but instead is concentrated at the axis of the tube, it tends to exhibit a highly arcuate or crescent-shaped meniscus profile. In that event it will take longer to remove individual fractions at the exit end of the column and intermingling of the stratified layers may occur.

Additionally, at the exit end of the column, it is desirable to have the minimum possible volume between the end of the column packing and the exit tube leading to the chromatographic analyzer. Each increment of volume in the exit passage contributes to the widening of the detection band on the chromatographic read out and tends to obscure trace element peaks that may be small with respect to a major component of the sample and that may occur at a closely spaced location relative to a major component peak in the chromatographic read out.

Conventionally, the packed chromatographic columns are sealed at each end with a uniformly porous disc, usually stainless steel, placed at the very end of the column tube. One common method is to press the discs into a terminating assembly or fitting. Another technique provides a counter bore at the end of the column and the terminator disc elements are mounted directly into the counter bore at the end of the tube. In either event, the inlet and outlet tubes connected to the chromatographic column typically have a very small bore relative to the inside diameter of the chromatographic column and it is necessary to provide some means of distributing the sample entering the column and of collecting the sample exiting the column. As mentioned, it is extremely important to provide a uniform flow profile over the entire face of the column both at the entrance end of the column from the very small bore of the inlet flow tube and also at the outlet or exit end of the column.

This distribution has been accomplished through the use of a distributor plate or small screen that permitted lateral flow between the wires of the screen. These screens typically were provided at both ends of the column, with the porous discs that were used to retain the packing within the chromatographic columns being positioned between the screens and the column packing.

In my copending application, Ser. No. 272,996 filed June 12, 1981 and entitled Chromatographic Column Assembly, there is disclosed a heterogeneous duplex-layer structure that eliminates the need for a distribution screen. The multi-layer structure with its uniquely configured outer surface achieves a uniform flow profile across the entire face of the chromatographic column despite the absence of the screen. The terminator element comprises a thin layer having a relatively low micron rating and a main body portion having a relatively higher micron rating and a coarse pimpled outer surface. The thin layer is secured to the planar surface of the amin body portion opposite the pimpled surface and faces toward the interior of the chromatographic column at either end thereof. The pimpled surface effectively facilitates lateral fluid flow of the sample relative to the main body portion to provide the requisite uniform profile across the entire face of the chromatographic column.

DISCLOSURE OF THE INVENTION

It has now been found that the use of a duplex layer structure can be obviated while at the same time providing an improvement in the efficiency of operation of the chromatographic column. This is achieved through the utilization of a new and improved channeled, dual-density chromatographic column terminator element of the type described herein. This terminator element is a homogeneous, porous sintered metal member that comprises a relatively low density, high porosity, central disc portion, an integral relatively high density rim portion peripherally circumscribing the central portion and an interface zone that integrally joins the rim and central portions. The relatively flat faces of the rim and central portions are essentially coplanar but are separated and delineated by a recess or channel at the surface of the interface zone intermediate said coplanar faces. The integral porous element exhibits a permeability ratio between the central disc portion and the rim portion of at least 3:1. Additionally, the central portion exhibits a density up to about 70 percent of the density of solid material of the same composition while the density of the rim portion is greater than that of the central portion and is up to 95 percent of that of solid material of the same composition.

The outer rim of the new and improved terminator element provides an excellent seal with the packed tube of the chromatographic column to prevent side leakage. At the same time the element achieves improved distribution of the sample across the column and improved efficiency of the chromatographic column due to both the porosity differential between the central and rim portions and the channeled configuration of the terminator element.

These and related advantages, features, properties, and relationships of the invention will be in part obvious and in part pointed out more in detail hereinafter in connection with the following detailed description and accompanying drawing which set forth an illustrative embodiment and are indicative of the way in which the principles of the invention are employed.

BEST MODE FOR CARRYING OUT THE INVENTION

Figure 1:
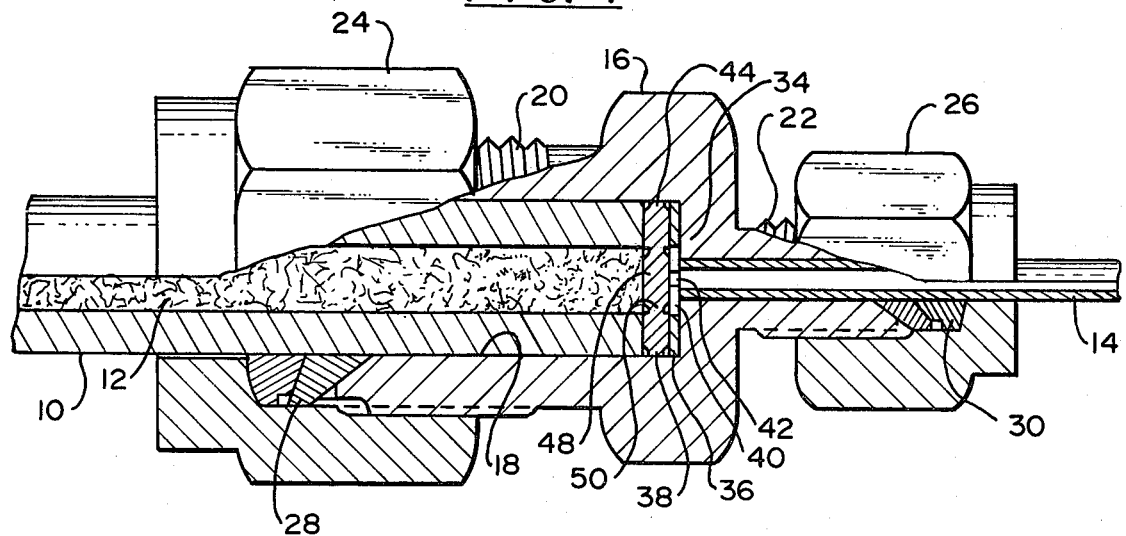
FIG. 1 is a side elevational view, partially broken away and partially in section, of one end assembly of a chromatographic column having a column terminator element of the present invention mounted therein.

Referring now to the drawings in greater detail wherein like reference numerals indicate like parts throughout the several figures, one end of a chromatographic column is shown in FIG. 1 with a terminator assembly mounted thereon. The column takes the form of a tubing 10, such as a stainless steel tubing, with its interior filled with a granular particulate absorbent material 12. A fluid flow tube 14 of substantially reduced diameter is connected to the end of the column by a suitable end fitting which, in the embodiment illustrated, is of the compression seal reducing type. This fitting includes a reducing union 16 adapted to receive the butt ends of both the column tubing 10 and the flow tube 14 within the coaxially extending stepped bore 18 thereof. The exterior of the union 16 is provided with threads 20, 22 on opposite ends thereof for engagement by the locking nuts 24, 26, respectively, that bear against and compress shim-like gaskets, generally designated 28, 30, abutting the opposite free ends of the union 16.

As illustrated, the bore 18 of the reducing union 16 is provided with an abrupt shoulder 34 between the small bore portion sized to receive the flow tube 14 and the opposite enlarged bore portion sized to receive the substantially larger tubing 10 of the chromatographic column. Mounted within the large bore portion at the shoulder 34 and abutting thereagainst is a distributor plate 36 and a chromatographic column terminator element 38 constructed in accordance with the present invention. The plate 36 can be of the well known type mentioned hereinbefore or of other suitable design. The plate 36 illustrated in FIG. 1 is a solid metal member provided with a star aperture comprised of a series of radially extending slots 40 all converging at a center opening 42. The radial slots 40 extend outwardly from the opening 42 a sufficient distance to provide full distribution of the fluid to the peripheral portion of the packing 12 within the column. Since the outside diameter of the flow tube 14 is typically less than the inside diameter of the chromatographic column, the plate 36 or other suitable separate or integral distributor is desirable to provide proper fluid distribution across the full extent of the terminator disc 38. In this way no portion of the sample is restricted in its flow at either end of the chromatographic column.

The terminator element 38 is a unitary one piece sintered metal frit of flat disc like configuration. It is substantially uniform in thickness and includes a porous metal outer rim portion 44 having an outside diameter substantially equal to the outside diameter of the tube 10 forming the chromatographic column. The rim portion 44 has a radial extent or dimension substantially equal to the thickness of the chromatographic column tubing 10 and is chamfered adjacent its periphery, as at 46, best shown in FIG. 3, to facilitate mounting the disc within the reducing union 16. The butt end of the chromatographic tubing 10 engages the rim portion 44 and bears against the terminator element 38 sandwiching it between the end of the tube and the plate 36. The compact porous metal frit construction of the rim portion 44 provides an excellent seal with the tubing 10 upon assembly within the end fritting.

Figure 3:
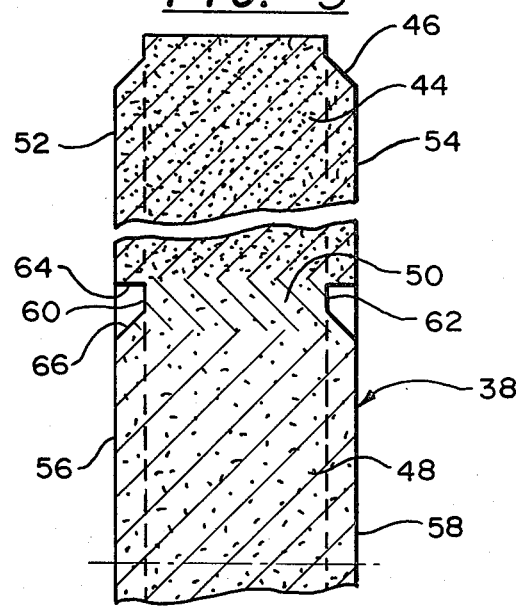
FIG. 3 is a substantially enlarged sectional view of a portion of the terminator element of FIG. 2 showing the interface zone between the central and rim portions of the column terminator element.
Figure 2:
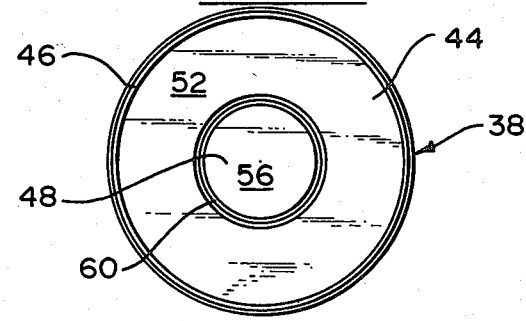
FIG. 2 is an enlarged plan view of the column terminator element used in the assembly of FIG. 1.

Integrally formed with the rim like portion 44 is a homogeneous, porous metal central disc portion 48 which, as best shown in FIG. 3, is integrally connected thereto through a narrow interface zone 50. The integral central disc portion 48 is of high porosity and exhibits a ratio of permeability relative to the outer rim portion 44 of at least 3:1; that is, the permeability flow rate of the central portion 48 is at least three times greater than that of the outer rim portion and preferably is about ten times greater. The central disc portion exhibits a low density, e.g. a density up to about 75 to 80 percent of the density of a solid of the same composition. The density preferably falls within the range of approximately 55–80 percent of the density of its corresponding solid material with the preferred density being about 65–70 percent.

The density of the outer ring portion 44, on the other hand, is always greater than that of the central disc portion 48 and therefore it exhibits a substantially reduced permeability. Its density falls within the range of about 80–95 percent of the density of its corresponding solid material of the same composition. Thus, for stainless steel having a solid density of 7.98 g/cc., the density of the outer ring portion will fall within the range of 5.5–7.5 g/cc., while the density of the central disc portion will be between about 4.0 and 6.0 g/cc. As will be appreciated, the higher density outer ring will have a smaller average pore size, typically within the range of 0.01–5.0 microns while the pore size in the central disc portion falls within the range of 1–10 microns. Of course, the pore size of the various portions of the terminator element may vary widely so long as the minimum ratio of permeability is maintained and the terminator element effectively and efficiently operates to provide the minimum possible volume retention between the end of the chromatographic column and the flow tube leading to the chromatographic analyzer.

As mentioned, the central disc portion is integrally connected to the rim portion of the terminator element through an interface zone 50 that predominantly exhibits the characteristics of the central disc portion 48, yet possesses characteristics that fall between those of the abutting central disc portion 48 and outer rim portion 44 of the terminator element. As best shown in FIG. 3, the opposite planar surfaces 52, 54 of the central disc portion and the corresponding planar surfaces 56, 58 of the outer rim are flat and coplanar but are interrupted by a circular recess or channel located on each planar surface of the element at the interface zone. The cross-sectional configuration of the channels 60, 62 respectively may vary both in depth and configuration. However, as shown, it is preferred that the channels be located so that when mounted within the terminator assembly they will be positioned at the periphery of the column packing 12.

The channels provided on both planar surfaces of the terminator element reduce the thickness of the element at that location by approximately 10–15 percent. This construction will permit slight flooding of the recess on the upstream side of the element while the reduction in thickness facilitates more rapid discharge of the fluid at the downstream or exit end thereby minimizing the "meniscus effect" and providing a more uniform flow profile and distribution of the sample across the full cross-sectional dimension of the column coupled with improved efficiency of operation. Additionally, since the permeability characteristics of the interface zone are more closely akin to those of the high porosity central disc portion, the fluid will rapidly pass through the terminator element and assure a minimum possible volume retention between the end of the packed column and the flow tube of the assembly.

In the specific embodiment depicted in FIG. 3, the channels 60, 62 provides a sharp or abrupt recess wall, such as wall 64 adjacent the ring portion 44 of the element. In fact the wall 64 is disposed perpendicular to planar surface 52. The wall of the channel adjacent the inner disc portion 48 is a tapered or chamfered wall such as wall 66 thereby providing increased surface area abutting portion 48. While it is not clear that this configuration provides a substantial improvement over other possible configuration, it has been found that this construction, when coupled with the permeability ratio between the central and rim portions, provides an improvement in efficiency of about 10 percent relative to the structure described in my earlier copending application.

The entire terminator element is a porous structure preferably fabricated of the same metal composition with variations in the particle size of the raw material prior to sintering and compaction or compression being responsible for the differences in performance characteristics between the central disc portion and the outer rim portion thereof. The element is fabricated in accordance with known procedures and is preferably made from stainless steel, although other materials such as bronze, copper, nickel, monel metal, inconel, hastelloy, or precious metals such as silver, gold or platinum may also be used.

As mentioned, the relative degree or ratio of permeability of the two portions of the terminator element and their relative densities have been used as a basis of comparison between the two distinct portions of the terminator element. These differences blend somewhat in the interface zone and the properties therein are difficult to measure. The outer rim typically is fabricated from stainless steel powder of a finer particle size so that upon compression and sintering, the outer rim will exhibit a desired higher density and lower permeability than the central portion that is fabricated from stainless steel powder having a larger particle size.

As can be seen from the foregoing detailed description, the present invention provides a new and improved chromatographic column terminator element having a unique dual denisty construction and improved efficiency of operation. The entire terminator element is a porous sintered metal disc but the different portions thereof exhibit a permeability differential of at least 3 to 1. The element can be rapidly and effectively incorporated into the terminator assembly of the column to achieve not only the desired stratified separation of the chromatographic sample but also improved sealing characteristics between the assembly and the column tube. This prevents any side leakage while undesirable sample volume retention is obviated by the highly permeable character of the central disc portion.

As will be apparent to persons skilled in the art, various modifications, adaptations and variations of the foregoing specific disclosure can be made without departing from the teachings of the present invention.

I claim:

1. A chromatographic column terminator element for use in a fitting connecting a chromatographic column with an end flow tube comprising an integral dual density porous frit disc including a relatively high density porous rim portion, an integral relatively low density porous central portion and a porous interface zone integrally joining said rim and central portions, the spaced faces of the rim and central portions of the disc being substantially planar, the surface at said interface zone being recessed relative to said planar faces, the permeability of said central portion relative to said rim portion being at least 3 to 1, the density of the central portion being up to about 80 percent of solid material of the same composition, the density of the rim portion being up to 95 percent of solid material of the same composition.

2. The terminator element of claim 1 wherein the central portion of the porous disc is a sintered metal portion that is substantially homogeneous throughout and exhibits a density of 55–80 percent of solid material of the same composition, the interface zone is a radially narrow portion relative to the central and rim portions and is positionable at the perimeter of the chromatographic column when mounted within the fitting.

3. The terminator element of claim 1 wherein the rim portion peripherally circumscribes the central portion and is adapted to be compressively engaged by a chromatographic column tubing when mounted within the fitting, the radial extent of the rim portion is substantially equal to the thickness of the chromatographic column tubing with the inner boundary thereof being substantially coincident with the surface recess of the interface zone.

4. The terminator element of claim 1 wherein the recessed surface of the interface zone reduces the thickness of the element by up to about 15 percent at that zone, at least a portion of the recessed surface facing the interior of the chromatographic column and being positioned at the perimeter of the column.

5. The terminator element of claims 1, 3, or 4 wherein the central portion exhibits a density of about 55–80 percent of solid material of the same composition and the rim portion exhibits a density of about 80–95 percent of solid material of the same composition, the permeability ratio of the central portion to the rim portion is at least about 10 to 1, and the density of the interface zone is substantially the same as that of the central portion.

6. The terminator element of claims 1, 2, 3 or 4 wherein the average pore size in the central portion is 1–10 microns and in the rim portion is 0.01–5.0 microns, the permeability ratio of the central portion to the rim portion being at least about 10 to 1.

7. The terminator element of claim 6 wherein the central portion is homogeneous throughout and exhibits a density of about 65–70 percent of solid material of the same composition, the central and rim portions have substantially coplanar surfaces on opposite sides of element and the interface zone is provided with recesses on opposite planar surfaces that interrupt the coplanar surfaces and reduce the thickness of the element by 10–15 percent at the interface zone.

8. A chromatographic column terminator assembly comprising the terminator element of claim 7 and a fitting adapted to connect a chromatographic column with an end flow tube.

9. The assembly of claim 8 including fluid distributor means intermediate said terminator element and said end flow tube.

* * * * *